United States Patent [19]

Shono et al.

[11] Patent Number: 5,120,406

[45] Date of Patent: Jun. 9, 1992

[54] PROCESSES FOR PREPARATION OF POLYSILANE

[75] Inventors: Tatsuya Shono; Shigenori Kashimura, both of Kyoto; Ryoichi Nishida, Ikoma; Shinichi Kawasaki, Osaka, all of Japan

[73] Assignee: Osaka Gas Company Limited, Osaka, Japan

[21] Appl. No.: 642,309

[22] Filed: Jan. 18, 1991

[30] Foreign Application Priority Data

Jan. 18, 1990 [JP] Japan ........................... 2-9947
Jun. 15, 1990 [JP] Japan ........................... 2-158225

[51] Int. Cl.$^5$ ............................................. C25B 3/00
[52] U.S. Cl. ............................ 204/59 QM; 204/59 R
[58] Field of Search ............... 204/59 R, 59 QM, 73 R

[56] References Cited

U.S. PATENT DOCUMENTS 4,933,053  6/1990  Tieke ........................... 204/59 QM

OTHER PUBLICATIONS

Biran, C., "Electrosynthesis, A Convenient Route to di—and Polysilanes", J. Organomet. Chem. 382 (3), C17-C20 (1990).

Fry, A. J., et al., "Electrochemical Synthesis of (α-Halobenzyl) Silanes and Benzal Disilanes", J. Org. Chem., 54, 4829-4832, 1989.

Hengge, E., et al., "An Electrochemical Method for the Synthesis of Silicon-Silicon Bonds", J. Organomet. Chem. 212, 155-161, (1981).

Chemical Abstract 113:240125q Shono et al., (1990).
Chemical Abstract 112:147728h Biran et al., (1990).

Primary Examiner—John Niebling
Assistant Examiner—Steven P. Marquis
Attorney, Agent, or Firm—Larson and Taylor

[57] ABSTRACT

The invention provides:

(1) a process for preparing a polysilane, comprising subjecting a halosilane to an electrochemical reaction using an anode of magnesium, copper or aluminum;

(2) a process for preparing a polysilane, comprising subjecting a halosilane to an electrochemical reaction under sonication using an anode of magnesium, copper or aluminum;

(3) a process for preparing a polysilane, comprising subjecting a halosilane to an electrochemical reaction using one electrode of magnesium, copper or aluminum and the other electrode of an electroconductive material which is the same as or different from magnesium, copper or aluminum while changing over the electrode polarity at a specific time interval; and (4) a process for preparing a polysilane, comprising subjecting a halosilane to an electrochemical reaction under sonication using one electrode of magnesium, copper or aluminum and the other electrode of an electroconductive material which is the same as or different from magnesium, copper or aluminum while changing over the electrode polarity at a specific time interval.

74 Claims, No Drawings

PROCESSES FOR PREPARATION OF POLYSILANE

BACKGROUND OF THE INVENTION

1. Field of the Invention

The present invention relates to processes for preparing a polysilane.

2. Prior Art

Polysilanes are drawing attention for their use as precursors of ceramics or as optoelectronic materials. A process for preparing a polysilane is known wherein dialkyldichloro-silane, dichlorotetraalkyldisilane or the like dissolved in toluene is stirred at a temperature of 100° C. or higher for an extended time period using an alkali metal such as metallic sodium to achieve reductive coupling (J. Am. Chem. Soc., 103 (1981) 7352). The process, however, has drawbacks. The process involves severe reaction conditions (e.g., a long period of heating), is incapable of controlling the molecular weight, and poses a serious problem of safety because of large amount of alkali metal used in manufacture on a commercial scale.

To overcome these drawbacks, a process has been proposed which is carried out under moderate conditions by subjecting dialkyldichlorosilane or the like to an electroreduction at room temperature (J. Organomet. Chem., 212 (1981) 155). The proposed process is conducted using mercury or cadmium as an anode and platinum, mercury, lead, titanium or iron as a cathode in a H-shaped cell equipped with a diaphragm and employing tetra-n-butylammonium perchlorate as a supporting electrolyte and 1,2-dimethoxyethane as a solvent. The electroreduction process has been expected to have potential capabilities of obviating the foregoing problems and effectively controlling the molecular weight and the distribution of molecular weight. However, the process has been unable to produce substances identifiable as polysilanes.

SUMMARY OF THE INVENTION

We conducted extensive research to resolve the above problems of conventional techniques, and found that the prior art problems can be substantially obviated or significantly mitigated by subjecting a halosilane to an electrochemical reaction using a specific metal as an anode.

Our further discovery was that the reaction efficiency can be markedly improved by changeover of the polarity of electrodes at a specific time interval in the electrochemical reaction.

Our additional finding was that when the reactor or the reaction mixture is sonicated in the foregoing electrochemical reaction, the reaction time is markedly shortened and the reaction product is produced in increased yields.

According to the present invention, there are provided the following processes for preparing a polysilane:

(i) a process for preparing a polysilane which comprises subjecting a halosilane to an electrochemical reaction using an anode of magnesium, copper or aluminum, the halosilane being represented by the formula

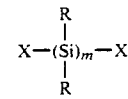
(1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, giving a polysilane represented by the formula

(2)

wherein R is as defined above and n is 10 to 11000;

(ii) a process for preparing a polysilane which comprises subjecting a halosilane to an electrochemical reaction under sonication using an anode of magnesium, copper or aluminum, the halosilane being represented by the formula

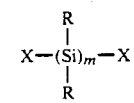
(1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, giving a polysilane represented by the formula

(2)

wherein R is as defined above and n is 10 to 11000;

(iii) a process for preparing a polysilane which comprises subjecting a halosilane to an electrochemical reaction using one electrode of magnesium, copper or aluminum and the other electrode of an electroconductive material which is the same as or different from magnesium, copper or aluminum while changing over the polarity of electrodes at a specific time interval, the halosilane being represented by the formula

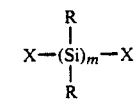
(1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, giving a polysilane represented by the formula

 (2)

wherein R is as defined above and n is 10 to 11000; and (iv) a process for preparing a polysilane which comprises subjecting a halosilane to an electrochemical reaction under sonication using one electrode of magnesium, copper or aluminum and the other electrode of an electroconductive material which is the same as or different from magnesium, copper or aluminum while changing over the polarity of electrodes at a specific time interval, the halosilane being represented by the formula

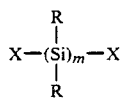 (1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, giving a polysilane represented by the formula

 (2)

wherein R is as defined above and n is 10 to 11000.

DETAILED DESCRIPTION OF THE INVENTION

The processes as defined above in items (i) to (iv) are hereinafter referred to as processes (i) to (iv), respectively.

The halosilane used as the starting material in any of the processes (i) to (iv) is represented by the formula

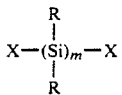 (1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom.

The reaction product obtained in any of the processes (i) to (iv) is a polysilane represented by the formula

 (2)

wherein R is as defined above and n is 10 to 11000.

In the formula (1), m is 1 to 3, and R represents a hydrogen atom, amino group or organic substituents. These R groups are the same or different. Stated more specifically, when m is 1, two R groups are the same or different; when m is 2, four R groups are the same or different; and when m is 3, six R groups are the same or different. Preferred compounds of the formula (1) are those in which m is 1 or 2. Examples of the alkyl group are those having 1 to 10 carbon atoms among which those of 1 to 6 carbon atoms are desirable. Examples of the aryl group include, for example, phenyl group, phenyl group substituted with at least one alkyl group of 1 to 6 carbon atoms, p-alkoxyphenyl group, etc. Examples of the alkoxy group are those having 1 to 10 carbon atoms among which those of 1 to 6 carbon atoms are preferred. When R groups are an amino group or organic substituents, at least one of hydrogen atoms may be substituted with the other functional group such as alkyl, aryl or alkoxy group.

In the formula (1), X is a halogen atom such as chlorine, fluorine, bromine and iodine atoms among which chlorine atom is preferred.

In the processes of the invention, the species of halosilane of the formula (1) are usable singly or at least two of them can be used in mixture. It is preferable to use a halosilane of the highest possible purity. For example, a preferred halosilane is one dried over calcium hydride and distilled.

For the reaction, the halosilane is dissolved in a solvent before use. Examples of useful solvents include a wide range of aprotic solvents. Specific examples of useful aprotic solvents are propylene carbonate, acetonitrile, dimethylformamide, dimethylsulfoxide, 1,2-dimethoxyethane, bis(2-methoxyethyl)ether, p-dioxane, tetrahydrofuran, methylene chloride, etc. These solvents are usable singly or at least two of them can be used in mixture. Preferably ether solvents such as 1,2-dimethoxyethane, bis(2-methoxyethyl)ether, p-dioxane, tetrahydrofuran and the like are usable singly or can be used in combination with other solvents. Among them, more preferable are 1,2-dimethoxyethane and tetrahydrofuran. Too low a concentration of the halosilane in the solvent reduces the current efficiency, whereas too high a concentration thereof may fail to dissolve the supporting electrolyte. A suitable concentration of the halosilane in the solvent is about 0.05 to about 20 mols/l preferably about 0.2 to about 15 mols/l more preferably about 0.3 to about 13 mols/l.

Examples of supporting electrolytes useful in the invention are sodium perchlorate, lithium perchlorate and like alkali metal perchlorates; lithium tetrafluoroborate and like alkali metal tetrafluoroborates; tetra-n-butylammonium chloride and like tetraalkylammonium halides; tetra-n-butylammonium perchlorate and like tetraalkylammonium perchlorates; tetra-n-butylammonium tetrafluoroborate and like tetraalkylammonium tetrafluoroborates; etc. These supporting electrolytes are usable singly or at least two of them can be used in mixture. Among the examples, preferred are lithium perchlorate, lithium tetrafluoroborate, tetra-n-butylammonium perchlorate and tetra-n-butylammonium tetrafluoroborate among which lithium perchlorate and tetra-n-butylammonium perchlorate are most desirable. Too low a concentration of the supporting electrolyte in the solvent imparts a reduced ionic conductivity to the reaction mixture, thus failing to achieve a satisfactory reaction progress, whereas too high a concentration thereof leads to excessive quantity of current applied, failing to obtain the electrode potential required for the reaction. A suitable concentration of the supporting electrolyte in the solvent is about 0.05 to about 5 mols/l, preferably about 0.1 to about 3 mols/l more preferably about 0.15 to about 1.2 mols/l.

An anode of magnesium, copper or aluminum or an alloy predominantly containing these metals is used in the process (i). Cathode materials are not limited insofar as an electric current can flow. Preferred cathode materials can be any of magnesium, copper, zinc, tin, aluminum, nickel and cobalt and alloys predominantly containing these metals. Preferred anode materials are magnesium, copper and alloys predominantly containing them among which magnesium is most preferred. The electrode form is not specifically limited insofar as an electric current can stably flow. Preferred examples of the form are rods, plates, tubes, coiled plates, etc. It is desirable to remove an oxide film from the electrode surface to a maximal extent before use. The removal of oxide film from the electrode can be effected by any desired method, as by washing the electrode with an acid and then with ethanol and ether and drying it under reduced pressure, by polishing the electrode in a nitrogen atmosphere, by conducting a combination of these methods, etc.

In carrying out the process (i), the halosilane of the formula (1), the supporting electrolyte and the solvent are charged into a sealable reactor having an anode and a cathode disposed therein. Subsequently an electrochemical reaction is conducted by passing a specific amount of electric current preferably with stirring by mechanical or magnetic means. The interior of the reactor has a dry atmosphere, preferably an atmosphere of dry nitrogen or inert gas, more preferably a deoxidized atmosphere consisting of dry nitrogen or inert gas. A current is passed in an amount of at least 1 F/mol based on halogen atoms in the halosilane. The molecular weight can be controlled by adjusting the amount of current applied. Optionally after a polysilane produced by use of at least 0.1 F/mol of electricity is separated as a product from the reaction system, the remaining halosilane may be recovered for reuse. The reaction time is variable depending on the amount of the halosilane used, the resistance of the electrolytic solution associated with the supporting electrolyte, the molecular weight of the desired polysilane, etc., and is suitably determined as required. The reaction temperature is in the range lower than the boiling point of the solvent used. The process (i) is advantageous in that the procedure is simplified by the absence of a diaphragm which is essential to use in conventional electrode reduction reactions.

The process (ii) is substantially the same as the process (i) except that the reactor or the reaction mixture is sonicated in the electrochemical reaction. The method of sonication is not specifically limited, and is carried out as by dipping the reactor in a ultrasonic bath, by disposing an ultrasonic vibration element in the reactor, etc. A preferred frequency of supersonic wave is about 10 to about 70 kHz. The output of sonication is suitably determinable depending on the reaction conditions including the type of starting materials, the amount of reaction mixture, the shape and dimensions of reactor and electrodes, the type of materials for electrodes and the surface area of electrodes, etc. A suitable output is about 0.01 to about 24 kW per 1 liter of the reaction mixture. The sonication markedly reduces the reaction time to ⅓ to ⅔ the reaction time required in the reaction done without sonication. In the process (ii), the solution is properly stirred by sonication alone or, when required, in combination with mechanical means.

In the process (iii), the reaction is performed in the same manner as in the process (i) with the exception of using one electrode of magnesium, copper or aluminum or an alloy predominantly containing such metals and the other electrode of an electroconductive material (such as nickel or cobalt) which is the same as or different from the above materials, and effecting the changeover of electrode polarity at a specific time interval. The changeover of electrode polarity stabilizes the current value which results in smooth progress of reaction, thereby reducing the reaction time with respect to a specific quantity of electricity used. The changeover of electrode polarity is carried out at a time interval of about 0.01 second to about 60 minutes, preferably about 1 second to about 10 minutes, more preferably about 10 seconds to about 3 minutes. For the changeover of the polarity, the use of two electrodes made of the same type of metals is preferred in the synthesis of a high molecular weight polysilane because the use thereof permits metallic ions (e.g. $Mg^{2+}$) to dissolve out and migrate between the electrodes, thereby decreasing the consumption of electrode, and allowing the current to flow for an extended period. The process (iii) can also dispense with a diaphragm.

In the process (iv), the reactor or the reaction mixture is sonicated in the electrochemical reaction. The process (iv) is substantially the same as the process (iii) with the exception of conducting sonication. The sonication is conducted in the process (iv) in the same manner as in the process (ii). In the process (iv), the changeover of electrode polarity and sonication in combination shortens the reaction time and increases the yield. When required, mechanical stirring means can be used in addition in the process (iv).

In the practice of the invention, it is desirable to remove the water from the solvent and the supporting electrolyte before their use in order to prevent the incorporation of oxygen in the main chain of the polysilane. For example, when tetrahydrofuran or 1,2-dimethoxyethane is used as a solvent, the solvent is preferably dried over sodium/benzo-phenone ketyl or the like before use. The removal of water from the supporting electrolyte is preferably conducted by drying with heating under reduced pressure or by addition of a substance (such as trimethylchlorosilane or the like) which easily reacts with water and which is easily removable.

The polysilane of the formula (2) prepared according to the invention has an average molecular weight of about 1000 to about 1 million (namely n=about 10 to about 11000 in the formula (2)).

The processes of the present invention can be also used for the preparation of other silane compounds.

For example, when a halosilane represented by the formula (3) shown below is subjected to an electrochemical reaction according to any of the processes (i) to (iv), a disilane represented by the formula (4) shown below can be synthesized.

wherein $R_1$, $R_2$ and $R_3$ are the same or different and each represent a hydrogen atom, an alkyl group, an aryl group, an alkoxy group or an amino group, and X is a halogen atom.

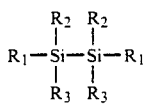   (4)

wherein $R_1$, $R_2$ and $R_3$ are as defined above.

For another example, when a silane compound represented by the formula (5) shown below is subjected to an electrochemical reaction according to any of the processes (i) to (iv), a polymer can be synthesized which is represented by the formula (6) shown below and which contains Si-Si bonds in the main chain.

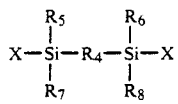   (5)

wherein $R_4$ is an aromatic group, an unsaturated aliphatic group, a group $-(CH_2)_m-$ or a group $-(CH_2-CH_2-O)_m$ (wherein m is 1 to 20), and $R_5$, $R_6$, $R_7$ and $R_8$ are the same or different and each represent a hydrogen atom, an alkyl group, an aryl group, an alkoxy group or an amino group, and X is a halogen atom.

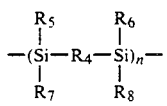   (6)

wherein $R_4$, $R_5$, $R_6$, $R_7$ and $R_8$ are as defined above, and n is 10 to 10000.

According to the present invention, the following remarkable results can be achieved.

(a) Since the processes of the invention do not use mercury or cadmium as an electrode, a polysilane can be produced with safety and ease without the risk of causing environmental pollution.

(b) Since the processes of the invention do not employ an alkali metal, a polysilane can be produced with safety and ease even on a commercial scale.

(c) The molecular weight of a polysilane to be produced can be controlled by adjusting the quantity of electricity applied.

(d) The formation of Si—O—Si bonds in the main chain can be effectively prevented.

(e) The absence of a diaphragm eliminates the problem of clogging in diaphragm, thereby serving to simplify the operation.

(f) The reaction time can be significantly shortened and the yield can be exceedingly improved when sonication is conducted in the electrochemical reaction.

EXAMPLES

Examples are given below to clarify the features of the present invention in further detail.

EXAMPLE 1

A 0.64 g quantity of anhydrous lithium perchlorate was fed to a 30 ml-vol. three-necked flask (hereinafter referred to as "reactor") equipped with a three-way cock and two magnesium electrodes (1 cm × 1 cm × 5 cm; washed sequentially with a dilute sulfuric acid, ethanol and ether, dried under reduced pressure and polished in a nitrogen atmosphere to eliminate an oxide film from the electrode surface). Over a period of 6 hours, the contents of the reactor were heated at 50° C. under the internal pressure reduced to 1 mm·Hg, thereby drying the lithium perchlorate. Dry nitrogen was charged into the reactor after removal of oxygen from the reactor. Then 15 ml of tetrahydrofuran was dried over sodium-benzophenone ketyl and added. A 0.97 ml quantity of methylphenyldichlorosilane dried over calcium hydride and distilled was added with a syringe. While the reactor was maintained at room temperature by a water bath, an electric current was applied by a constant-voltage source. While the polarity of the two electrodes was changed over every one minute with use of a commutator, an electric current was applied for about 96 hours to pass 5.4 F/mol of electricity based on the chlorine content of the methylphenyldichlorosilane.

After completion of the reaction, 150 ml of a 1N solution of hydrochloric acid was added to the reaction mixture and the resulting mixture was extracted with ether, followed by reprecipitation from 2-propanol and tetrahydrofuran.

The reaction gave a polysilane having a weight-average molecular weight of 5540. The oxygen content of the polysilane was up to 0.1%, which confirmed a very low content of oxygen in the main chain.

EXAMPLE 2

An electrochemical reaction was conducted in the same manner as in Example 1 with the exception of using 7.5 ml of tetrahydrofuran and applying 4.8 F/mol of electricity based on the chlorine content of methylphenyldichlorosilane.

The reaction gave a polysilane having a weight-average molecular weight of 21900.

EXAMPLE 3

An electrochemical reaction was carried out by the same procedure as in Example 1 with the exception of using 1.5 g of 1,2-dichlorotrimethylphenyldisilane as the starting material represented by the formula (1) and applying 4.4 F/mol of electricity based on the chlorine content. The application of electric current continued for about 168 hours.

The reaction produced a polysilane having a weight-average molecular weight of 11400 in a yield of 5%.

EXAMPLE 4

An electrochemical reaction was conducted in the same manner as in Example 1 with the exception of using methyl-n-hexyldichlorosilane as the starting material of the formula (1).

The reaction gave the corresponding polysilane.

EXAMPLE 5

An electrochemical reaction was effected in the same manner as in Example 1 with the exception of using dimethoxydichlorosilane as the starting material of the formula (1).

The reaction gave the corresponding polysilane.

EXAMPLE 6

An electrochemical reaction was conducted in the same manner a in Example 1 with the exception of using methyl-p-biphenyldiohlorosilane as the starting material of the formula (1).

The reaction gave the corresponding polysilane.

EXAMPLE 7

An electrochemical reaction was carried out using methylphenyldichlorosilane in the same manner as in Example 1 except that a magnesium electrode (1 cm × 1 cm × 5 cm) was used as an anode and a nickel electrode (1 cm × 0.1 cm × 5 cm) as a cathode without changeover of the electrode polarity.

The reaction gave a polysilane similar to that prepared in Example 1.

EXAMPLE 8

An electrochemical reaction was performed using methylphenyldichlorosilane by the same procedure as in Example 1 with the exception of using copper electrodes (1 cm × 0.1 cm × 5 cm) as an anode and a cathode.

The reaction gave a polysilane similar to that obtained in Example 1.

EXAMPLE 9

An electrochemical reaction was conducted using methylphenyldichlorosilane in the same manner as in Example 1 with the exception of using tetra-n-butylammonium perchlorate as a supporting electrolyte.

The reaction gave a polysilane similar to that obtained in Example 1.

EXAMPLE 10

An electrochemical reaction was effected using methylphenyldichlorosilane by the same procedure as in Example 1 with the exception of using, as a solvent, 15 ml of 1,2-dimethoxyethane dried over sodium-benzophenone ketyl.

The reaction gave a polysilane similar to that obtained in Example 1.

EXAMPLE 1

An electrochemical reaction was carried out by the same procedure as in Example 1 with the exception of using 1.94 ml of methylphenyldichlorosilane and applying 3.2 F/mol of electricity based on the chlorine content. The passage of current continued for about 118 hours.

After completion of the reaction, the reaction mixture was subjected to reprecipitation from ethanol and benzene, giving a polysilane having a weight-average molecular weight of 8960 in a yield of 22%.

EXAMPLE 12

An electrochemical reaction was conducted in the same manner as in Example 11 except that the reactor was dipped in an ultrasonic washer (output of 60 W, frequency of 45 kHz) and that 4.0 F/mol of electricity based on the chlorine content was applied. The application of current continued for about 85 hours.

After completion of the reaction, the reaction mixture was subjected to reprecipitation from ethanol and benzene, giving a polysilane having a weight average molecular weight of 9780 in a yield of 33%.

EXAMPLE 13

An electrochemical reaction was effected in the same manner as in Example 3 except that the reactor was dipped in an ultrasonic washer (output of 60 W, frequency of 45 kHz) and that 4.0 F/mol of electricity based on the chlorine content was applied. The application of electric current continued for about 72 hours.

After completion of the reaction, the reaction mixture was subjected to reprecipitation from ethanol and benzene, giving a polysilane having a weight-average molecular weight of 8100 in a yield of 15%.

EXAMPLE 14

An electrochemical reaction was carried out by the same procedure as in Example 12 with the exception of using aluminum electrodes (1 cm × 0.1 cm × 5 cm) as an anode and a cathode. A polysilane having a weight-average molecular weight of 8700 was produced in a yield of 15%.

EXAMPLE 15

An electrochemical reaction was conducted in the same manner as in Example 12 with the exception of drying the anhydrous lithium perchlorate over trimethylchlorosilane.

After completion of the reaction, the reaction mixture was subjected to reprecipitation from ethanol and benzene, giving a polysilane having a weight-average molecular weight of 11500 in a yield of 65%.

EXAMPLE 16

An electrochemical reaction was conducted in the same manner as in Example 12 with the exception of using 3.9 ml of methylphenyldichlorosilane and 4.0 ml of tetrahydrofuran and applying 0.4 F/mol of electricity based on the chlorine content.

After completion of the reaction, the reaction mixture was subjected to reprecipitation from ethanol and benzene, giving a polysilane having a weight-average molecular weight of 55500 in a yield of 15%.

COMPARISON EXAMPLE 1

An electrochemical reaction was carried out using methylphenyldichlorosilane in a reactor having no diaphragm in the same manner as in Example 12 with the exception of using platinum electrodes (1 cm × 1 cm × 0.1 cm) as an anode and a cathode.

After completion of the reaction, the reaction mixture was subjected to reprecipitation from ethanol and benzene. However, substantially no precipitate was obtained.

This result reveals that when an electrochemical reaction is conducted using platinum electrodes in a reactor having no diaphragm, generally the reaction gave a polysilane having a weight-average molecular weight of only up to 800.

We claim:

1. A process for preparing a polysilane which comprises subjecting a halosilane to an electrochemical reaction in a reactor having no diaphragm using an anode of magnesium, copper, aluminum or alloys thereof, the halosilane being represented by the formula

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, the electric current during the electrochemical reaction being in an amount of at least 1 F/mol based on halogen atoms in the halosilane, giving a polysilane represented by the formula

  (2)

wherein R is as defined above and n is 10 to 11000.

2. A process according to claim 1 wherein m in the halosilane of the formula (1) is 1 or 2.

3. A process acccording to claim 1 wherein R in the halosilane of the formula (1) is an alkyl group having 1 to 10 carbon atoms.

4. A process according to claim 3 wherein R in the halosilane of the formula (1) is an alkyl group having 1 to 6 carbon atoms.

5. A process according to claim 1 wherein R in the halosilane of the formula (1) is an aryl group selected from the group consisting of phenyl group, phenyl group substituted with at least one alkyl group of 1 to 6 carbon atoms, and p-alkoxyphenyl group.

6. A process according to claim 5 wherein R in the halosilane of the formula (1) is a p-alkoxyphenyl group having 1 to 10 carbon atoms.

7. A process according to claim 6 wherein R in the halosilane of the formula (1) is a p-alkoxyphenyl group having 1 to 6 carbon atoms.

8. A process according to claim 1 wherein X in the halosilane of the formula (1) is chlorine.

9. A process according to claim wherein the concentration of the halosilane is in an aprotic solvent in the range of about 0.05 to about 20 mols/l.

10. A process according to claim 9 wherein the concentration of the halosilane in the aprotic solvent is in the range of about 0.2 to about 15 mols/l.

11. A process according to claim 1 wherein a supporting electrolyte is used which is selected from the group consisting of lithium perchlorate, lithium tetrafluoroborate, tetra-n-butylammonium perchlorate and tetra-n-butylammonium tetrafluoroborate.

12. A process according to claim 11 wherein the supporting electrolyte is lithium perchlorate or tetra-n-butylammonium perchlorate.

13. A process according to claim 11 wherein the concentration of the supporting electrolyte in the solvent is about 0.05 to about 5 mols/l.

14. A process according to claim 13 wherein the concentration of the supporting electrolyte in the solvent is 0.1 to about 3 mols/l.

15. A process according to claim 14 wherein the concentration of the supporting electrolyte in the solvent is 0.15 to about 1.2 mols/l.

16. A process according to claim 1 wherein the anode is made of a material selected from magnesium, copper, alminum and alloys predominantly containing these metals.

17. A process according to claim 16 wherein the anode is made of magnesium or an alloy thereof.

18. A process for preparing a polysilane which comprises subjecting a halosilane to an electrochemical reaction in a reactor having no diaphragm under sonication using an anode of magnesium, copper, aluminum or alloys thereof, the halosilane being represented by the formula

  (1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, the electric current during the electrochemical reaction being in an amount of at least 1 F/mol based on halogen atoms in the halosilane, giving a polysilane represented by the formula

  (2)

wherein R is as defined above and n is 10 to 11000.

19. A process according to claim 18 wherein the frequency of supersonic wave is about 10 to about 70 kHz.

20. A process according to claim 18 wherein m in the halosilane of the formula (1) is 1 or 2.

21. A process according to claim 18 wherein R in the halosilane of the formula (1) is an alkyl group having 1 to 10 carbon atoms.

22. A process according to claim 21 wherein R in the halosilane of the formula (1) is an alkyl group having 1 to 6 carbon atoms.

23. A process according to claim 18 wherein R in the halosilane of the formula (1) is an aryl group selected from the group consisting of phenyl group, phenyl group substituted with at least one alkyl group of 1 to 6 carbon atoms, and p-alkoxyphenyl group.

24. A process according to claim 23 wherein R in the halosilane of the formula (1) is a p-alkoxyphenyl group having 1 to 10 carbon atoms.

25. A process according to claim 24 wherein R in the halosilane of the formula (1) is a p-alkoxyphenyl group having 1 to 6 carbon atoms.

26. A process according to claim 18 wherein X in the halosilane of the formula (1) is chlorine.

27. A process according to claim 18 wherein the concentration of the halosilane is in an aprotic solvent in the range of about 0.05 to about 20 mols/l.

28. A process according to claim 27 wherein the concentration of the halosilane in the aprotic solvent is in the range of about 0.2 to about 15 mols/l.

29. A process according to claim 18 wherein a supporting electrolyte is used which is selected from the group consisting of lithium perchlorate, lithium tetrafluoroborate, tetra-n-butylammonium perchlorate and tetra-n-butylammonium tetrafluoroborate.

30. A process according to claim 29 wherein the supporting electrolyte is lithium perchlorate or tetra-n-butylammonium perchlorate.

31. A process according to claim 29 wherein the concentration of the supporting electrolyte in the solvent is about 0.05 to about 5 mols/l.

32. A process according to claim 31 wherein the concentration of the supporting electrolyte in the solvent is 0.1 to about 3 mols/l.

33. A process according to claim 32 wherein the concentration of the supporting electrolyte in the solvent is 0.15 to about 1.2 mols/l.

34. A process according to claim 18 wherein the anode is made of a material selected from magnesium, copper, aluminum and alloys predominantly containing these metals.

35. A process according to claim 34 wherein the anode is made of magnesium or an alloy thereof.

36. A process for preparing a polysilane which comprises subjecting a halosilane to an electrochemical reaction in a reactor having no diaphragm using one electrode of magnesium, copper aluminum or alloy thereof, and the other electrode of an electroconductive material which is the same as or different from magnesium, copper or aluminum, while changing over the polarity of electrodes at a specific time interval, the halosilane being represented by the formula

  (1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, the electric current during the electrochemical reaction being in an amount of at least 1 F/mol based on halogen atoms in the halosilane, giving a polysilane represented by the formula

  (2)

wherein R is as defined above and n is 10 to 11000.

37. A process according to claim 36 wherein the changeover of electrode polarity is carried out at a time interval of about 0.01 second to about 60 minutes.

38. A process according to claim 37 wherein the changeover of electrode polarity is carried out at a time interval of about 10 seconds to about 3 minutes.

39. A process according to claim 36 wherein m in the halosilane of the formula (1) is 1 or 2.

40. A process according to claim 36 wherein R in the halosilane of the formula (1) is an alkyl group having 1 to 10 carbon atoms.

41. A process according to claim 40 wherein R in the halosilane of the formula (1) is an alkyl group having 1 to 6 carbon atoms.

42. A process according to claim 36 wherein R in the halosilane of the formula (1) is an aryl group selected from the group consisting of phenyl group, phenyl group substituted with at least one alkyl group of 1 to 6 carbon atoms, and p-alkoxyphenyl group.

43. A process according to claim 42 wherein R in the halosilane of the formula (i) is a p-alkoxyphenyl qroup having 1 to 10 carbon atoms.

44. A process according to claim 43 wherein R in the halosilane of the formula (1) is a p-alkoxyphenyl group having 1 to 6 carbon atoms.

45. A process according to claim 36 wherein X in the halosilane of the formula (1) is chlorine.

46. A process according to claim 36 wherein the concentration of the halosilane is in an aprotic solvent in the range of about 0.05 to about 20 mols/l.

47. A process according to claim 46 wherein the concentration of the halosilane in the aprotic solvent is in the range of about 0.2 to about 15 mols/l.

48. A process according to claim 36 wherein a supporting electrolyte is used which is selected from the group consisting of lithium perchlorate, lithium tetrafluoroborate, tetra-n-butylammonium perchlorate and tetra-n-butylammonium tetrafluoroborate.

49. A process according to claim 48 wherein the supporting electrolyte is lithium perchlorate or tetra-n-butylammonium perchlorate.

50. A process according to claim 48 wherein the concentration of the supporting electrolyte in the solvent is about 0.05 to about 5 mols/l.

51. A process according to claim 50 wherein the concentration of the supporting electrolyte in the solvent is 0.1 to about 3 mols/l.

52. A process according to claim 51 wherein the concentration of the supporting electrolyte in the solvent is 0.15 to about 1.2 mols/l.

53. A process according to claim 36 wherein the anode is made of a material selected rom magnesium, copper, aluminum and alloys predominantly containing these metals.

54. A process according to claim 53 wherein the anode is made of magnesium or an alloy thereof.

55. A process for preparing a polysilane which comprises subjecting a halosilane to an electrochemical reaction in a reactor having no diaphragm under sonication using one electrode of magnesium, cooper, aluminum or alloys thereof, and the other electrode of an electroconductive material which is the same as or different from magnesium, copper, aluminum or alloys thereof, while changing over the polarity of electrodes at a specific time interval, the halosilane being represented by the formula

  (1)

wherein m is 1 to 3, R is a hydrogen atom, an alkyl group, an aryl group, an alkoxy group or an amino group, provided that 2 R groups are the same or different in case of m=1, 4 R groups are the same or different in case of m=2, and 6 R groups are the same or different in case of m=3, and X is a halogen atom, the electric current during the electrochemical reaction being in an amount of at least 1 F/mol based on halogen atoms in the halosilane, giving a polysilane represented by the formula

  (2)

wherein R is as defined above and n is 10 to 11000.

56. A process according to claim 55 wherein the frequency of supersonic wave is about 10 to about 70 kHz.

57. A process according to claim 55 wherein the changeover of electrode polarity is carried out at a time interval of about 0.01 second to about 60 minutes.

58. A process according to claim 57 wherein the changeover of electrode polarity is carried out at a time interval of about 10 seconds to about 3 minutes.

59. A process according to claim 55 wherein m in the halosilane of the formula (1) is 1 or 2.

60. A process according to claim 55 wherein R in the halosilane of the formula (1) is an alkyl group having 1 to 10 carbon atoms.

61. A process according to claim 60 wherein R in the halosilane of the formula (1) is an alkyl group having 1 to 6 carbon atoms.

62. A process according to claim 55 wherein R in the halosilane of the formula (1) is an aryl group selected from the group consisting of phenyl group, phenyl group substituted with at least one alkyl group of 1 to 6 carbon atoms, and p-alkoxyphenyl group.

63. A process according to claim 62 wherein R in the halosilane of the formula (1) is a p-alkoxyphenyl group having 1 to 10 carbon atoms.

64. A process according to claim 63 wherein R in the halosilane of the formula (1) is a p-alkoxyphenyl group having 1 to 6 carbon atoms.

65. A process according to claim 55 wherein X in the halosilane of the formula (1) is chlorine.

66. A process according to claim 55 wherein the concentration of the halosilane in the aprotic solvent is in the range of about 0.05 to about 20 mols/l.

67. A process according to claim 66 wherein the concentration of the halosilane in the aprotic solvent is in the range of about 0.2 to about 15 mols/l.

68. A process according to claim 55 wherein a supporting electrolyte is used which is selected from the group consisting of lithium perchlorate, lithium tetrafluoroborate, tetra-n-butylammonium perchlorate and tetra-n-butylammonium tetrafluoroborate.

69. A process according to claim 68 wherein the supporting electrolyte is lithium perchlorate or tetra-n-butylammonium perchlorate.

70. A process according to claim 68 wherein the concentration of the supporting electrolyte in the solvent is about 0.05 to about 5 mols/l.

71. A process according to claim 70 wherein the concentration of the supporting electrolyte in the solvent is 0.1 to about 3 mols/l.

72. A process according to claim 71 wherein the concentration of the supporting electrolyte in the solvent is 0.15 to about 1.2 mols/l.

73. A process according to claim 55 wherein the anode is made of a material selected from magnesium, copper, alminum and alloys predominantly containing these metals.

74. A process according to claim 73 wherein the anode is made of magnesium or an alloy thereof.

* * * * *